(12) United States Patent
Khouri et al.

(10) Patent No.: US 11,660,095 B2
(45) Date of Patent: May 30, 2023

(54) DEVICES AND METHODS FOR WOUND CLOSURE

(71) Applicant: Lipocosm, LLC, Key Biscayne, FL (US)

(72) Inventors: Roger K. Khouri, Key Biscayne, FL (US); Khalil R. Khouri, Key Biscayne, FL (US)

(73) Assignee: LIPOCOSM, LLC, Key Biscayne, FL (US)

( * ) Notice: Subject to any disclaimer, the term of this patent is extended or adjusted under 35 U.S.C. 154(b) by 50 days.

(21) Appl. No.: 17/097,969

(22) Filed: Nov. 13, 2020

(65) Prior Publication Data

US 2021/0059675 A1 Mar. 4, 2021

Related U.S. Application Data

(63) Continuation-in-part of application No. 16/882,443, filed on May 23, 2020, now Pat. No. 11,464,515.

(Continued)

(51) Int. Cl.
*A61B 17/02* (2006.01)
*A61B 17/22* (2006.01)
(Continued)

(52) U.S. Cl.
CPC .......... *A61B 17/08* (2013.01); *A61B 17/282* (2013.01); *A61B 17/2816* (2013.01); *A61B 17/2841* (2013.01); *A61B 2017/081* (2013.01)

(58) Field of Classification Search
CPC .... A61B 2017/2901; A61B 2017/2908; A61B 2017/2919; A61B 2017/291;
(Continued)

(56) References Cited

U.S. PATENT DOCUMENTS 5,814,067 A * 9/1998 Fleischmann .......... A61B 17/08 606/205
6,007,552 A 12/1999 Fogarty
(Continued)

FOREIGN PATENT DOCUMENTS

CN 103753417 A * 4/2014 ............... B25B 7/04
CN 204409054 U * 6/2015
CN 109009395 10/2020

OTHER PUBLICATIONS

Khouri, KS et al. Percutaneous Mesh Expansion: A Regerative Wound Closure Alternative. Plast Reconstr Surg, Feb. 2018, Journal of the American Society of Plastic Surgeons, vol. 141, No. 2, pp. 451-457. (Year: 2018).*

(Continued)

*Primary Examiner* — Timothy J Neal
*Assistant Examiner* — Mitchell Brian Hoag
(74) *Attorney, Agent, or Firm* — Neil D. Gershon

(57) ABSTRACT

A tissue approximation device for wound closure having a first arm having a proximal end and a distal end, a second arm having a proximal end and a distal end, the second arm connected to the first arm. A first rake member is connected to the distal end of the first arm and has a first plurality of tissue engaging members extending therefrom to engage tissue. A second rake member is attached to the distal end of the second arm, the second rake member having a second plurality of tissue engaging members extending therefrom to engage tissue. A transverse bar can extend through the first and second rake members such that the first and second rake members movable along the transverse bar. Systems and methods for wound closure are also disclosed.

17 Claims, 13 Drawing Sheets

Related U.S. Application Data

(60) Provisional application No. 62/852,288, filed on May 23, 2019.

(51) Int. Cl.
  *A61B 17/08* (2006.01)
  *A61B 17/28* (2006.01)

(58) Field of Classification Search
  CPC .... A61B 2017/2913; A61B 2017/2926; A61B 2017/2927; A61B 2017/2932; A61B 2017/2933; A61B 2017/294; A61B 2017/2944; A61B 17/08; A61B 17/2816; A61B 17/2841; A61B 17/282; A61B 2017/081; A61B 2017/00477; A61B 2017/00473
  See application file for complete search history.

(56) References Cited

U.S. PATENT DOCUMENTS

| | | | | |
|---|---|---|---|---|
| 6,206,896 | B1* | 3/2001 | Howell | A61B 17/1227 606/151 |
| 6,315,780 | B1* | 11/2001 | Lalonde | A61B 17/8866 606/86 R |
| 6,387,112 | B1* | 5/2002 | Fogarty | A61B 17/282 606/207 |
| 10,172,631 | B2* | 1/2019 | Tepic | A61B 17/1714 |
| 2009/0326578 | A1* | 12/2009 | Ewers | A61B 17/0401 606/213 |
| 2011/0118778 | A1* | 5/2011 | Burbank | A61B 17/320016 606/205 |
| 2012/0143241 | A1* | 6/2012 | Ray | A61B 17/062 606/205 |
| 2012/0296172 | A1 | 11/2012 | Raven | |
| 2013/0085341 | A1* | 4/2013 | Nobis | A61B 17/29 600/213 |
| 2014/0257035 | A1* | 9/2014 | Blain | A61B 5/389 600/104 |
| 2017/0000525 | A9* | 1/2017 | Basic | A61B 17/28 |
| 2019/0125390 | A1* | 5/2019 | Shelton, IV | F16D 27/09 |
| 2019/0142425 | A1* | 5/2019 | Smith | A61B 17/10 606/205 |
| 2020/0178964 | A1* | 6/2020 | Khristov | A61B 17/0482 |
| 2020/0281683 | A1* | 9/2020 | Ward | A61B 18/085 |

OTHER PUBLICATIONS

Khouri, KS et al. Percutaneous Mesh Expansion: A Regenerative Wound Closure Alternative. Plast Reconstr Surg, vol. 141, No. 2, Feb. 2018, pp. 451-457 [pdf online], [retrieved on Feb. 8, 2022]. Retrieved from the Internet <URL:https://journals.lww.com/plasreconsurg/Fulltext/2018/02000 > (Year: 2018).

Khouri, R., Khouri, K., &; Khouri, R. (2016). Percutaneous mesh expansion: A New Wound Closure Alternative. AAPS. Retrieved Feb. 8, 2022, from <U RL:https://meeting .aaps 1921.org/abstracts/2016/31.cgi> (Year: 2016).

\* cited by examiner

NORMAL RESTING STATE OF TISSUES

VERTICAL FIBERS UNDER TENSION WITH MAXIMAL SKIN ADVANCEMENT

PERCUTANEOUSLY INTRODUCED ARRAY OF NEEDLES SEVER THE TENSE VERTICAL FIBERS

FURTHER ADVANCEMENT MADE POSSIBLE AFTER DIVIDING THE V. FIBERS

Wound defect place under tension

Oscillating needle inflicting a pattern of staggered alternating slits in the tensed tissue Mesh expansion of the slits allows wound edges to advance Healing tissue regenerates and fills the gaps between slits Tensionless closure of wound defect by mesh expansion of tensed wound edges

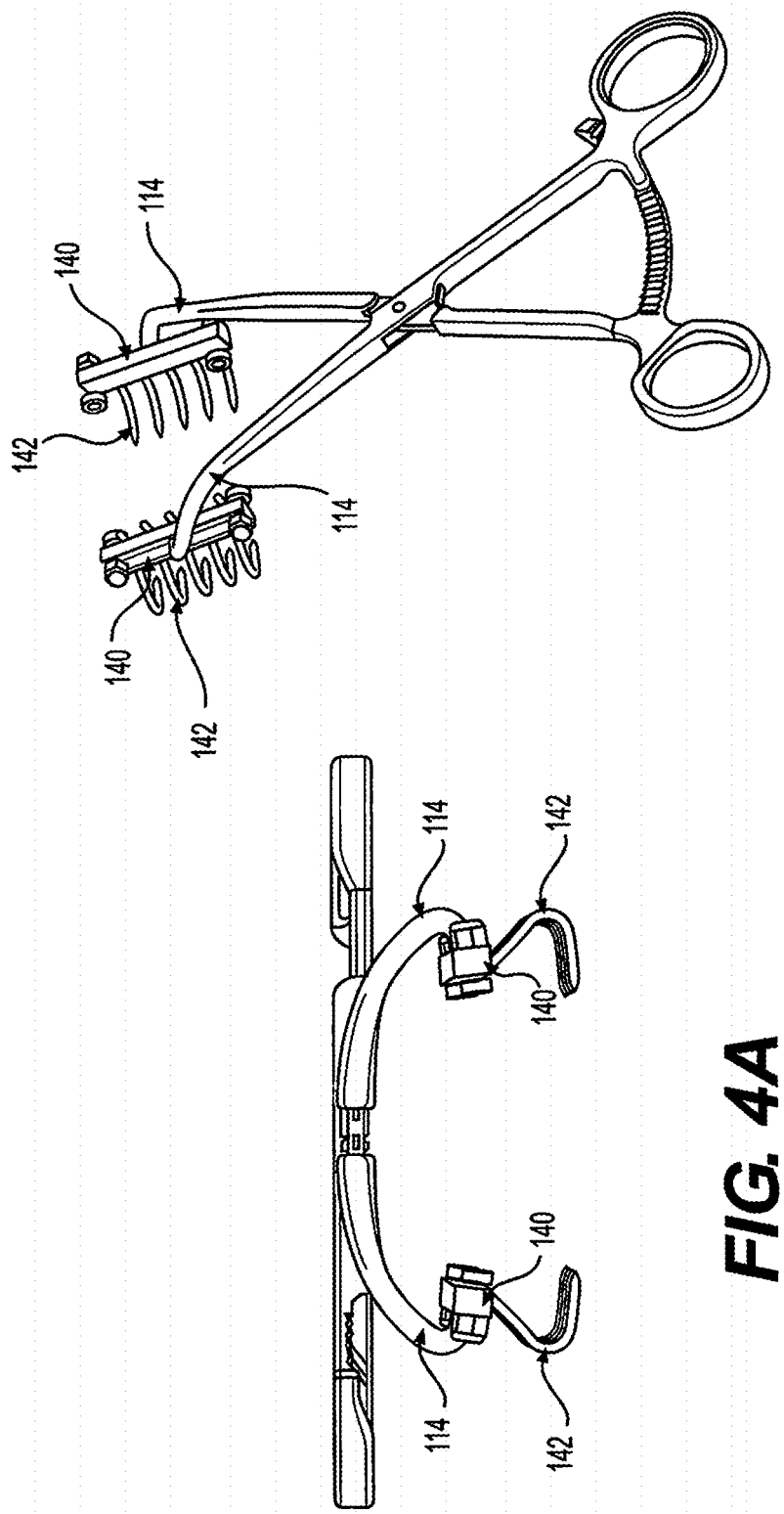

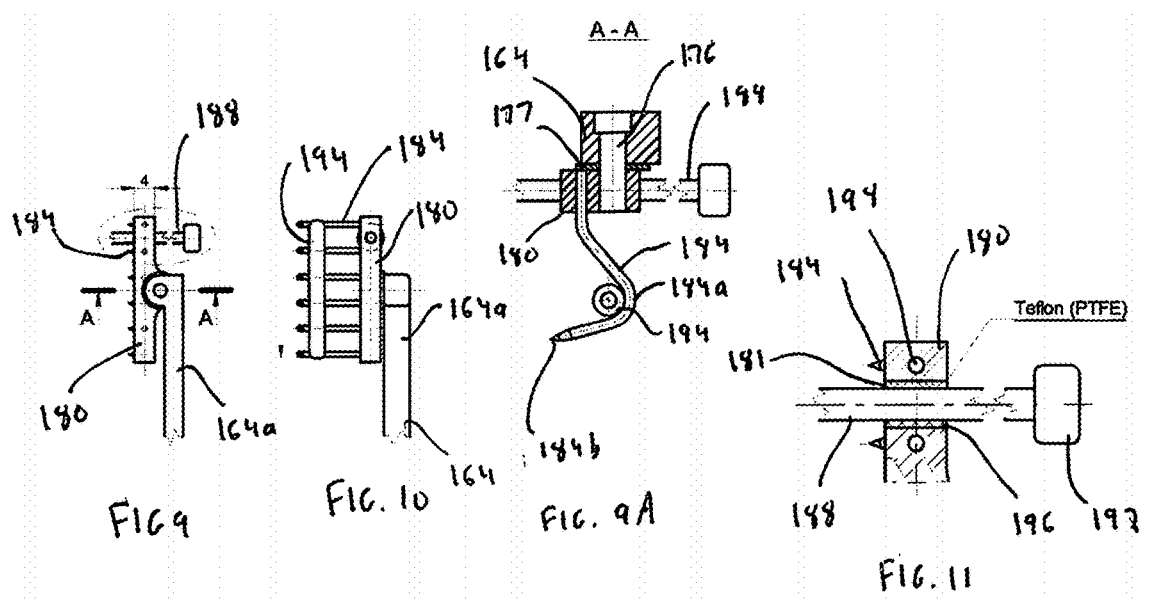

DEVICES AND METHODS FOR WOUND CLOSURE

CROSS-REFERENCE TO RELATED APPLICATION

This application is a continuation in part of application Ser. No. 16/882,443, filed May 23, 2020, which claims the benefit of priority of U.S. Provisional Patent Application No. 62/852,288, filed May 23, 2019. The entire contents of each of these applications are incorporated herein by reference.

TECHNICAL FIELD

The present disclosure relates to surgical devices and methods for wound closure and corresponding methods for performing reconstructive surgical procedures.

BACKGROUND

Surgical wounds can be left to heal by themselves (secondary intention healing), or they can be closed surgically. Secondary intention healing of a wound can take weeks to months depending on the size and location of the wound. In many cases, scars are formed after healing of the wound. In some situations, surgical closure is preferred over secondary intention healing when it can accelerate the healing process, protect the underlying tissues (e.g., bone, cartilage, nerve), improve skin function by choosing the direction of skin tension on the wound edges (e.g., avoiding ectropion), and/or improve cosmesis by hiding the scar on the wound edges as much as possible.

Typical surgical techniques to close a wound include primary closure, skin graft, and flap tissue transfers. Large wounds with edges that cannot be approximated without applying excessive tension usually require skin grafts or flap tissue transfers for closure. However, these procedures often result in residual disfiguring scars, carry significant morbidity, and give the final appearance of a patch. Therefore, there is a need for devices and methods that allow for safe closure of large wounds without or with reduced residual scars.

SUMMARY

The present disclosure provides a device, system and/or method that overcomes the deficiencies of the prior art. The present disclosure provides a tissue approximation device that grips tissue on opposing edges (sides) of a wound and approximates the tissue edges. Various embodiments of the tissue approximation device, including structure that maintains a parallel orientation and movement of the tissue gripping structure of the tissue approximation device, are disclosed in detail below.

The tissue approximation device is configured in preferred embodiments to be used with a meshing device (tissue mesher) that creates small needle holes to release the restrictive fibrous structures in the tissue. An example of such tissue mesher is described in detail below. In such system, the approximation device approximates the edges of the wound and places them under high tension in order to facilitate the tissue mesher needles to sever the restrictive taut fibers outside the approximated region of tissue to mesh expand the surrounding tissues and allow for a tension free closure, as described below.

According to an exemplary embodiment of the present disclosure, a tissue approximation device is described. In some embodiments, the tissue approximation device includes a first scissors arm having a proximal end and a distal end and a second scissors arm having a proximal end and a distal end. In some embodiments, the second scissors arm is connected to the first scissors arm at a pivot point. In some embodiments, the tissue approximation device further includes a first rake member connected to the distal end of the first scissors arm via a first articulating joint. In some embodiments, the first rake member includes a plurality of hooks configured to grip tissue. In some embodiments, the tissue approximation device further includes a second rake member connected to the distal end of the second scissors arm via a second articulating joint. In some embodiments, the second rake member includes a plurality of hooks configured to grip tissue. The arms can be moved in a scissors like fashion or in a parallel fashion in alternate embodiments.

According to an exemplary embodiment of the present disclosure, a kit or system for closing a wound is described. In some embodiments, the kit includes a tissue approximation device and a meshing device. In some embodiments, the tissue approximation device is configured to apply tension to tissue in an area of interest for closing the wound. In some embodiments, the tissue approximation device includes a first scissors arm having a proximal end and a distal end and a second scissors arm having a proximal end and a distal end. In some embodiments, the second scissors arm is connected to the first scissors arm at a pivot point. In some embodiments, the tissue approximation device further includes a first rake member connected to the distal end of the first scissors arm via a first articulating joint. In some embodiments, the first rake member includes a plurality of hooks configured to grip tissue. In some embodiments, the meshing device includes at least one puncturing device configured to puncture the tissue. The meshing device creates a plurality of punctures in tissue while the approximation device tightens them such that the punctures can inflict a mesh expansion pattern that can expand the surrounding tissues and gradually approximate the ends (edges) of the wound without undue tension.

According to an exemplary embodiment of the present disclosure, a method for closing a wound is described. In some embodiments, the method includes applying tension to tissue in an area of interest for closing the wound using a tissue approximation device. In some embodiments, the method further includes meshing the tissue while under the tension using a meshing device. In some embodiments, the method further includes releasing at least a portion of the tension. In some embodiments, the method includes bringing the wound edges together under tension using the tissue approximation device. In some embodiments, the method further includes relieving the tension by inflicting a staggered pattern of alternating punctures using the meshing device to mesh expand the restrictive tissue to achieve a tensionless closure of the wound defect.

In accordance with another embodiment of the present disclosure, a tissue approximation device is provided comprising a first arm having a proximal end and a distal end and a second arm having a proximal end and a distal end, wherein the second arm is connected to the first arm. A first rake member is connected to the distal end of the first arm and has a first plurality of tissue engaging members, e.g., hooks, extending therefrom to engage, e.g., grip, tissue. A second rake member is attached to the distal end of the second arm and has a second plurality of tissue engaging members, e.g., hooks, extending therefrom to engage, e.g., grip, tissue. A transverse bar extends through the first and second rake members, the first and second rake members movable along the transverse bar that maintains the rakes parallel to each other.

In some embodiments, the first rake member is connected to the distal end of the first arm via a first articulating joint and the second rake member is connected to the distal end of the second arm via a second articulating joint. In some embodiments, the first and second arms are pivotably connected and move in scissors-like fashion.

In some embodiments, the first rake member and the second rake member are movable towards each other in a parallel movement to move the tissue edges closer together as the distal ends of the first arm and the second arm are approximated.

In some embodiments, the hooks of the rake members each have a curved portion. A second bar can be provided on the hooks, wherein the second bar is spaced from tips of the hooks to provide a stop to limit tissue penetration of the hooks. The second bar can be parallel to the transverse bar.

In some embodiments, the first rake member includes a first channel and the second rake member includes a second channel, and the transverse bar extends through the first and second channels and maintains a parallel orientation of the first and second rake members as the first and second rake members slide along the transverse bar toward each other to approximate tissue.

In some embodiments, a coating is provided within the first and second channels engageable by the transverse bar such that the coating constrains the transverse bar and prevents a wedging effect that could impair smooth gliding through the channels. In some embodiments, the coating is Teflon, although other materials that can facilitate friction free gliding and perpendicular alignment are also contemplated. In other embodiments, a plurality of rollers are provided in or outside the channel to engage, constrain and provide friction free gliding of the transverse bar. A plurality of springs can be provided in or adjacent the channel in lieu of or in addition to the rollers to engage/constrain the transverse bar and similarly prevent wedge locking that could limit even gliding. In each of these embodiments, the first and second rake members can move toward each other along the transverse bar in a parallel orientation.

In some embodiments, the transverse bar is positioned at a distal region of the first and second rake members and is perpendicular to a longitudinal axis of the rake members. While remaining perpendicular to the longitudinal axis of the rake members, the transverse bar could be located at any region of the rake members.

In accordance with another aspect of the present disclosure, a system for closing a wound is provided comprising a tissue approximation device and a meshing device. The tissue approximation device is configured to apply tension to tissue in an area of adjacent the wound, the tissue approximation device having a first arm having a proximal end and a distal end and a second arm having a proximal end and a distal end, the second arm being connected to the first arm. A first rake member is connected to the distal end of the first arm and has a first plurality of tissue engaging members, e.g., hooks, extending therefrom configured to grip tissue on a first side of the wound and a second rake member is connected to the distal end of the second arm and has a second plurality of tissue engaging members, e.g., hooks, extending therefrom configured to grip tissue on a second side of the wound. The first and second arms are movable to move the first and second rake members toward each other to adjust a distance between the first and second rake members to approximate tissue. The meshing device has at least one puncturing member configured to puncture the tissue, the meshing device puncturing tissue outside a region of tissue defined between the first and second rake members.

In some embodiments, the tissue approximation device includes a transverse bar extending through the first and second rake members, the first and second rake members movable in a parallel fashion along the transverse bar.

In some embodiments, the first rake member includes a first channel and the second rake member includes a second channel, the transverse bar extending through the first and second channels and maintaining a parallel orientation of the first and second rake members as the first and second rake members slide along the transverse bar toward each other to approximate tissue.

In accordance with another aspect of the present disclosure, a method for closing a wound is provided comprising:

a) placing a tissue approximation device adjacent a wound so a first rake member extending from a first arm is positioned on a first side of the wound and a second rake member extending from a second arm is positioned on a second side of the wound, the first and second rake members spaced apart a first distance from each other;

description that follows.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain exemplary principles of certain disclosed embodiments as set forth in the accompanying claims. In the drawings, like reference numerals identify similar structural features of the devices throughout the several views.

BRIEF DESCRIPTION OF THE DRAWINGS

FIG. 4A illustrates a front view of the tissue approximation device of FIG. 3A.

FIG. 4B illustrates a perspective view of the exemplary tissue approximation device of FIG. 3A.

FIG. 9 is a close up view of the distal end of the first arm and rake of the tissue approximation device of FIG. 7.

FIG. 9A is a cross-sectional view taken along line A-A of FIG. 9.

FIG. 10 is a close up view of the distal end of the first arm and the rake of the tissue approximation device of FIG. 7.

FIG. 11 is a cross-sectional view of a portion of the rake of the tissue approximation device of FIG. 7 showing the transverse bar extending through a channel in the rake, the channel having a coating.

DETAILED DESCRIPTION

Figure 1A:
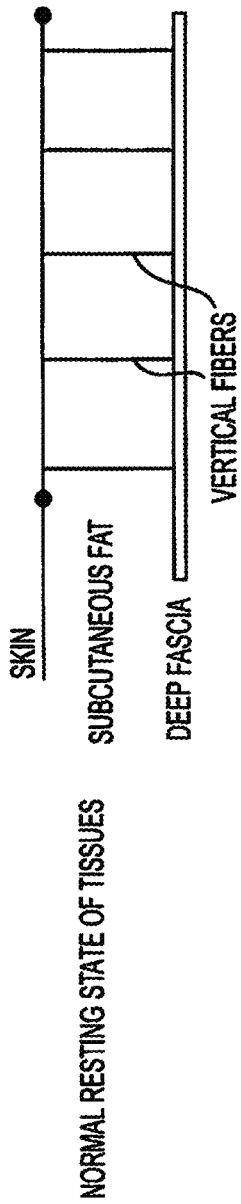
FIGS. 1A-1D illustrate an exemplary technique for releasing restrictive fibrous structures in tissue placed under tension.

The present disclosure provides a device, system and/or method that enhances wound closure as it avoids disfiguring scars and reduces morbidity. This is facilitated by the tissue approximation device of the present disclosure that grips tissue on opposing edges (sides) of a wound and applies a tension that facilitates the mesh expansion effect of the tissue mesher needles. This mesh expansion allows the approximation device to approximate the tissue edges without undue tension. The devices include a pair of arms with opposing tissue engaging structures that move toward each other upon manipulation of the arms. Various embodiments of the tissue approximation device are discussed in detail below, including embodiments that include structure that maintains a parallel orientation and movement of the tissue engaging structure of the tissue approximation device. The tissue approximation device can in preferred embodiments be used in conjunction with a meshing device (tissue mesher) that creates small needle holes to release the restrictive fibrous structures in the tissue. The tissue approximation device can also be used in conjunction with other devices, systems and/or methods.

The devices and methods of the present disclosure use and/or enhance the regenerative ability of tissues to close wounds, do not require expensive equipment, and allow for minimal or at least reduced morbidity compared to existing devices and wound closing methods. In some embodiments, the present disclosure allows for the healing or closing of wounds without scars. In some embodiments, the present disclosure allows for the healing or closing of wounds without visible scars. In some embodiments, the present disclosure allows for the healing or closing of wounds with less scars than existing wound closure procedures do.

The inventors recognized that tissue can regenerate across tiny (e.g., 1 mm) gaps without forming a scar. The inventors further recognized that by creating a large number of these small gaps, wounds that would otherwise have required flaps or grafts can instead be closed by the approximation of scarless tissue regeneration.

According to some embodiments of the present disclosure, a method for wound closure is provided. In some embodiments, the method for wound closure uses a tissue approximation device to temporarily approximate the edges surrounding a wound and place the tissue in an area of interest under tension. As defined herein, the area of interest may include an area in the wound, an area surrounding the wound, or both. In some embodiments, a method for wound closure includes performing a surgical technique of percutaneous mesh expansion. In some embodiments, percutaneous mesh expansion is performed while the tissue in the area of interest is placed under tension by the tissue approximation device. In some embodiments, percutaneous mesh expansion is performed using a sharp needle or a meshing device comprising an array of needles.

The following section describes percutaneous mesh expansion according to some embodiments of the present disclosure. Various features and functions of the meshing device and the tissue approximation device according to some embodiments of the present disclosure are described in the sections that follow.

Percutaneous Mesh Expansion (PME)

The inventor developed PME as a regenerative wound closure procedure to reduce or minimize residual scars after a wound heals. The inventor developed this procedure based, at least in part, upon a discovery that needle puncture wounds in the 1 mm range, such as wounds caused by insertion of intravenous lines, typically heal without residual scars. In some embodiments, PME is performed by applying punctures to the tissue in an area of interest to release the restrictive fibrous structures in the tissue. The release of the restrictive fibrous structures allows the tissue to expand and facilitate the advancement of the tissue towards the wound, thereby closing the wound. In some embodiments, the punctures are applied in the form of stacked rows or arrays of punctures to the tissue.

As described herein, the term "tissue" refers to any types of soft tissue at and/or surrounding a wound site that that connect, support, or surround structures and organs of the body, not being hard tissue, such as bone. Tissue may include muscles, tendons, fat, fascia, skin, or any other type of soft tissue. As used herein, the term "meshing" refers to applying one or more punctures or stacked rows or arrays of punctures to a tissue to release the restrictive fibrous structures in the tissue. As used herein, the term releasing the restrictive fibrous structures in the tissue may include severing, nicking, or cutting the restrictive fibrous structures in the tissue. It is also recognized that needles can release the restrictive fibrous structures in the tissue that is placed under tension while sparing other structures in the tissue, such as nerves or blood vessels.

The inventor further discovered that punctures are more likely to release the restrictive fibrous structures in a tissue when the tissue is placed under tension. FIGS. 1A-1D illustrate an example of releasing vertical fibers by percutaneously meshing or puncturing a tissue placed under tension. As illustrated in FIG. 1A, restrictive fibrous structures connect the skin and the deep immobile tissue layers, such as the fascia underneath. These restrictive fibrous structures can be collectively called the subcutaneous aponeurosis.

Figure 1B:
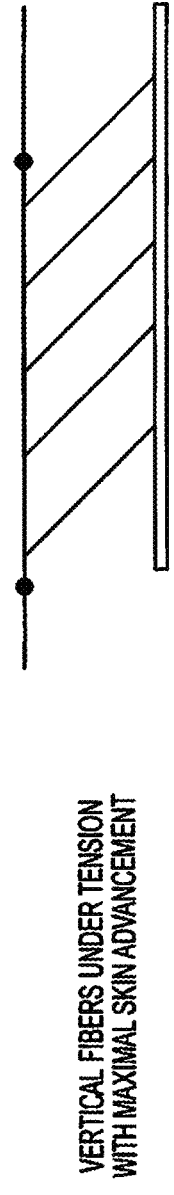
Figure 1C:
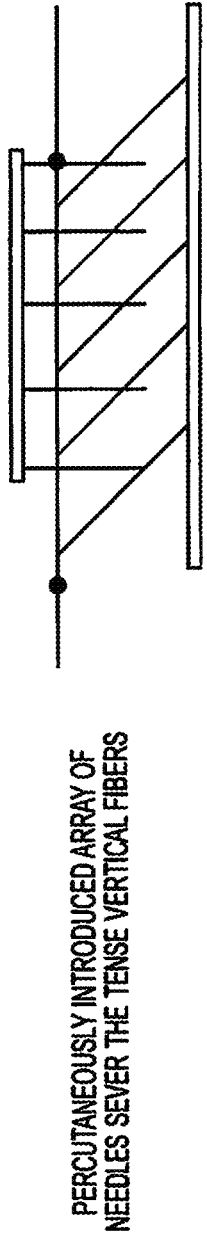
Figure 1D:
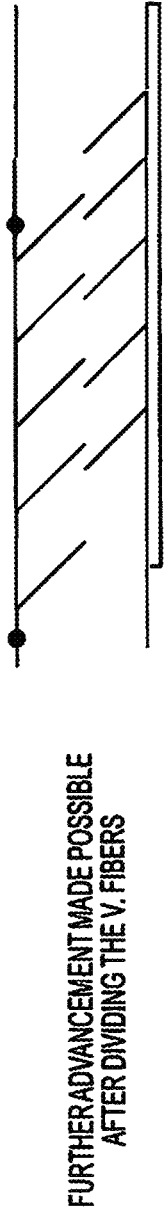

As illustrated in FIG. 1B, the restrictive fibrous structures impose a natural laxity limit to how much tissue can normally be advanced. As illustrated in FIG. 1C, applying tension to the skin to maximize advancement of the skin within the natural laxity limit of the subcutaneous aponeurosis places the restrictive fibrous structures under tension, rendering them more susceptible to being released by percutaneous meshing or punctures. When these restrictive fibrous structures are released as illustrated in FIG. 1D, tension is then reduced or released, and the tissue can then expand and advance beyond the natural laxity limit of the subcutaneous aponeurosis.

The inventor discovered that the release of the restrictive fibrous structures creates a fibrous vascularized scaffold with interstices that are later filled in by new tissue generated by the natural regenerative abilities of tissue. The filling of the interstices increases the volume of the tissue and causes the tissue to expand in the fibrous vascularized scaffold. Such tissue expansion further facilitates the advancement of tissue at and/or towards the wound. Therefore, the release of the restrictive fibrous structures allows the wound to be filled with naturally regenerated tissue instead of scar tissue to eventually close the wound. This process of tissue regeneration and expansion in a fibrous scaffold with interstices created by meshing the tissue is referred herein as "mesh expand" or "mesh expansion."

Figure 2A:
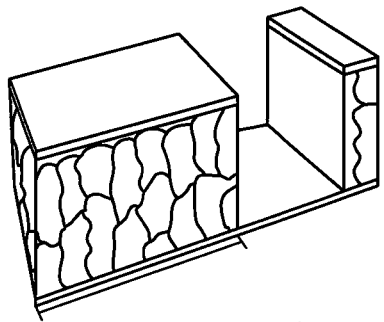
FIGS. 2A-2E illustrate an exemplary technique for closing a wound defect, according to some embodiments of the present disclosure.
Figure 2B:
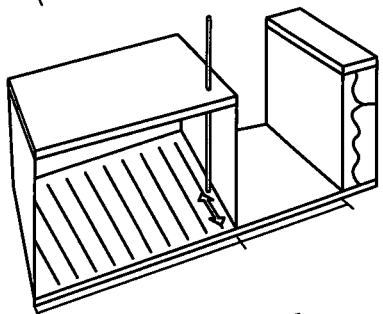
Figure 2C:
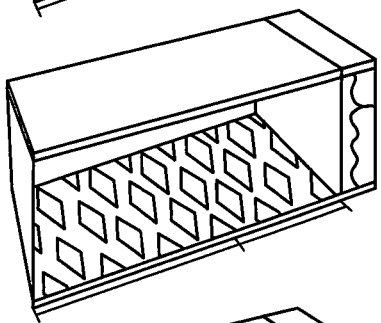
Figure 2D:
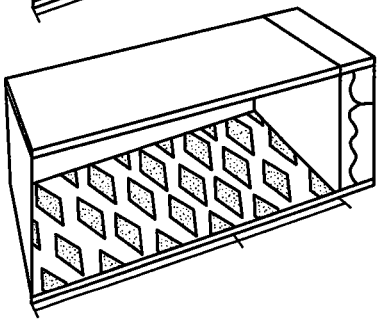
Figure 2E:
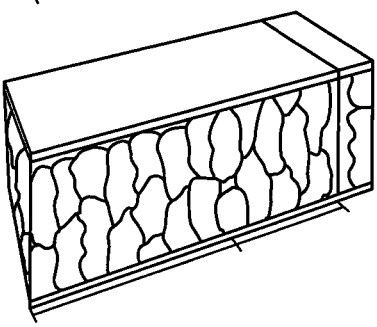

FIGS. 2A-2E illustrate an exemplary technique for closing a wound defect. FIG. 2A illustrates that the subcutaneous aponeurosis can restrict the approximation of the tightened wound edges. FIG. 2B illustrates using a needle to inflict a staggered pattern of alternating slits in the tissue under tension. In some embodiments, the needle is a needle with at least one cutting edge. In some embodiments, the needle is oscillated or moved back and forward to create a slit after punctuation. The slits created by the needle may release all or some of the tension in the tissue. FIGS. 2C and 2D illustrate that the slits allow the tissue to mesh expand by regenerating new tissue that fills the gaps between the slits. In some embodiments, the slits allow the tissue to mesh expand around and/or towards the wound edges. In some embodiments, the slits allow the tissue at and/or around the wound edges to mesh expand, thereby approximating the wound edges to achieve a tensionless closure.

The inventor further discovered that the size of the punctures and their spacing can affect the amount of tissue regeneration and/or expansion that can be achieved. Excessive meshing or punctures could destroy the local circulation, leading to ischemia and necrosis. Excessive meshing or punctures could also tear the deeper tissues and destroy the integrity of the fibrous vascularized scaffold, leading to the creation of undesirable cavities in the tissue. Therefore, the inventor found that the meshing ratio, that is the ratio of the amount of tissue that is punctured to the total amount of the tissue in an area of interest, needs to be judiciously determined to maintain a fibrous scaffold with sufficient capillary circulation while still allowing for tissue regeneration. In some embodiments, a meshing ratio ranging from 20% to 40% is used for meshing the tissue in an area of interest.

In some embodiments, the punctures are applied in a meshing pattern designed and gauged to create interstices for the tissue to naturally expand into using its regenerative abilities. In some embodiments, the punctures are applied in a meshing pattern designed and gauged to provide a recipient scaffold with interstices for receiving a regenerative graft material. In some embodiments, the meshing pattern includes an array of punctures spaced apart by 1 mm to 10 mm. In some embodiments, the meshing pattern includes an array of punctures arranged in one or more staggered rows. In some embodiments, the meshing pattern includes an array of punctures arranged in 2 to 6 staggered rows. In some embodiments, each puncture wound of the meshing pattern has a width or a diameter of 1 mm to 1.5 mm. In some embodiments, the interstices created by the punctures are filled by regenerated tissue over a period of healing time. In some embodiments, the interstices created by the punctures are filled with a material having regenerative potential. In some embodiments, the material having regenerative potential may be platelet rich plasma, physiological solutions containing growth factors, adipose tissue, stem cells or other types of cells, autografts, allografts, or a combination thereof.

In some embodiments, the interstices of the fibrous vascularized scaffold created by the meshing or puncturing provide a favorable graft to recipient interface where regenerative graft material can survive. Therefore, in some embodiments, the material having regenerative potential is a regenerative graft material. The regenerative graft material may be a man-made material, a naturally occurring material, or a material derived from a naturally occurring material. For example, the regenerative graft material may include an adipogenic material, a material derived from fat cells, a material derived from fat tissue, liposuctioned tissue, a material derived from liposuctioned tissue, adipose cells, stem cells, growth factors, or a selected combination thereof. The stem cells may include adipose-derived stems cells. The adipogenic material, material derived from fat tissue (whether autogenous or from allografts), liposuctioned tissue, or material derived from liposuctioned tissue may include adipose cells, adipose-derived stems cells, and/or growth factors.

In some embodiments, PME is performed to close a wound of large size. In some embodiments, the size of the wound ranges from 3 cm to 15 cm. In some embodiments, the size of the wounds that can be closed with this technique is limited by the available amount of normal peripheral tissue that can be safely meshed. In some embodiments, PME is performed to close the wound of a plastic surgery reconstruction site. In some embodiments, PME is performed to close the wound of a graft material harvesting site, such as a liposuction site. In some embodiments, PME is performed to close the wound of a reconstruction site that receives a graft material, such as a lipografting site. For example, PME may be performed to close the wound of a breast reconstruction site that receives a graft material. In some instances, PME is used to close the defect created by a transferred or advanced flap.

Performing the surgical technique of PME may include a series of procedures. In some embodiments, local or general anesthesia is performed. For example, tumescent epinephrine or lidocaine anesthesia may be performed at and/or around the wound. In some embodiments, after anesthesia is performed, the wound edges or the tissue in an area of interest are temporarily approximated and placed under tension using a tissue approximation device. Embodiments of the tissue approximation device are described in detail further below. Then, PME is performed to the tissue in the area of interest to release the restrictive fibrous structures in the tissue. In some embodiments, the area of interest for applying the PME is predetermined based on one or more considerations, which may include the size of the wound, the nature of the tissue in the area of interest, and the location of the wound. In some embodiments, a meshing pattern is predetermined based on one or more of these considerations.

In some embodiments, wound closure is performed without using the tissue approximation device to apply tension. The wound edges or the tissue in an area of interest are alternatively temporarily approximated with sutures under tension, such as retention sutures with subsequent full relief of the tension by the meshing, to facilitate perfusion of the edges and normal wound healing. In some embodiments, wound closure is performed before tension is fully relieved. In some embodiments, such wound closure is performed using the surgical technique of primary closure.

In some embodiments, the surgical technique of PME is performed to close the wound of a site for harvesting a graft material. In these embodiments, before performing PME, a graft material is retrieved from the wound. In some embodiments, the surgical technique of PME is performed to close the wound of a reconstructive site for receiving a graft material. In these embodiments, before performing PME, a graft material is injected or otherwise placed into the wound. In some embodiments, after performing PME, a material having regenerative potential is injected into the tissue in the area of interest to facilitate the expansion and advancement of the tissue for closing the wound.

Meshing Device

In some embodiments, PME is performed using a meshing device. In some embodiments, the meshing device includes at least one puncturing device. In some embodiments, the meshing device includes a supporting framework, and the at least one puncturing device is mounted on the supporting framework.

In some embodiments, the puncturing devices are needles. In some embodiments, the needles are cutting needles or hypodermic needles. In some embodiments, the puncturing devices are pins or rods with sharp cutting tips. In some embodiments, the puncturing devices are configured to be mounted on a supporting framework to have the same angle of penetration. In other embodiments, the puncturing devices are configured to be mounted on the supporting framework to have different angles of penetration.

In some embodiments, the puncturing devices have the same length. In such embodiments, the meshed tissue includes interstices distributed in one or two dimensions, which allows the expansion of a slice or a sheet of tissue. In other embodiments, the puncturing devices have different lengths. In such embodiments, the meshed tissue includes interstices distributed in three dimensions, which allows three-dimensional volumetric expansion of tissue. In some embodiments, the length of the puncturing devices ranges from 1 cm to 15 cm.

In some embodiments, the tissue mesher described in FIGS. 21-28 in International Patent Application No. PCT/US2013/039675 is used as the meshing device. International Patent Application No. PCT/US2013/039675 is incorporated herein by reference in its entirety.

Tissue Approximation Device

As described above, punctures are more likely to release the restrictive fibrous structures in the tissue in an area of interest when the tissue is placed under tension. Thus, in some embodiments, PME is performed after the tissue in the area of interest is placed under tension. In some embodiments, the tension is applied temporarily. Various methods may be used to place tissue under tension. According to some embodiments of the present disclosure, the tissue may be placed under tension generated by an internally or externally applied mechanical force. For example, a surgeon may insert retention sutures over protective bolsters, but this process takes time and consumes extra supplies. Alternatively, the surgeon may choose to use one of several commercially available tissue approximation devices. However, such devices are expensive and difficult to manipulate. Accordingly, some embodiments of the present disclosure provide a tissue approximation device that is more intuitive and ergonomic for surgeons to use than commercially available tissue approximation devices. Exemplary embodiments of the tissue approximation device are described below with reference to FIGS. 3A-13.

Note as used herein, the term "proximal" denotes components or portions of the device closer to the user and the term "distal" denotes components or regions further from the user.

Figure 3A:
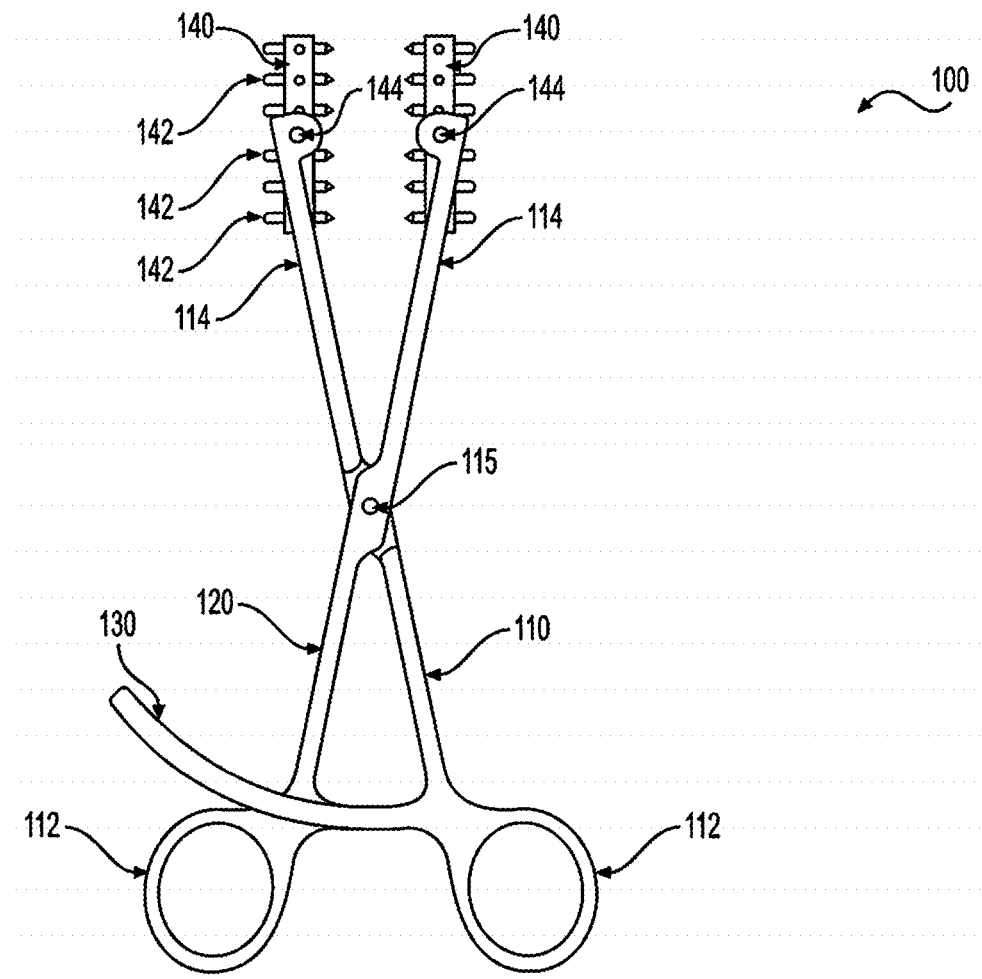
FIG. 3A illustrates an exemplary tissue approximation device, according to some embodiments of the present disclosure.
Figure 3B:
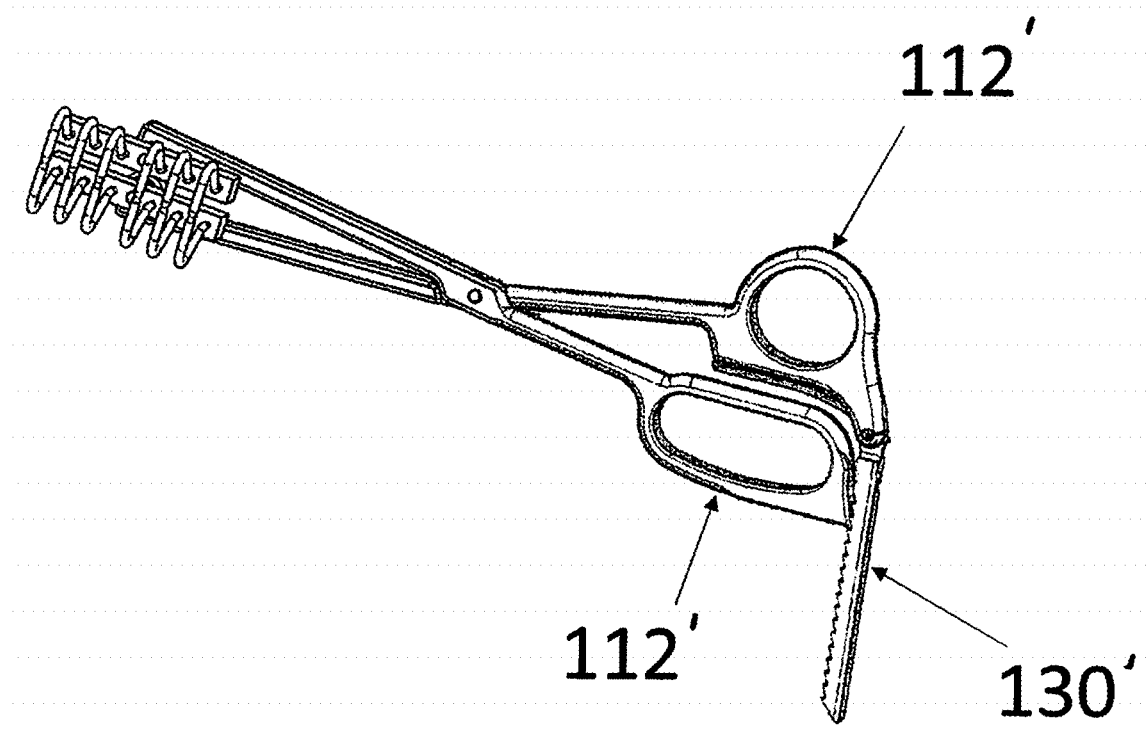
FIG. 3B illustrates an exemplary tissue approximation device, according to some embodiments of the present disclosure.
Figure 3C:
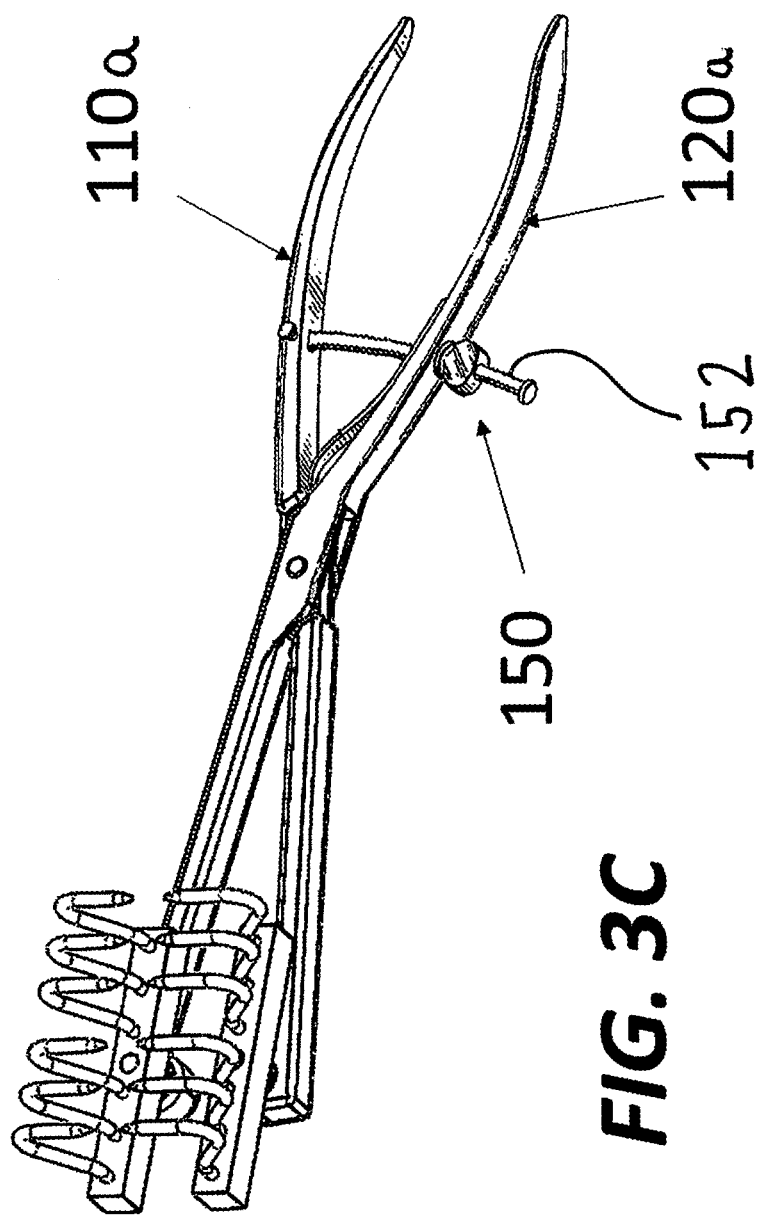
FIG. 3C illustrates an exemplary tissue approximation device, according to some embodiments of the present disclosure.

FIG. 3A is a schematic representation of a tissue approximation device 100, according to some embodiments of the present disclosure. As shown in FIG. 3A, in some embodiments, tissue approximation device 100 includes a first scissors arm 110 pivotally connected to a second scissors arm 120 at a pivot point 115 (also called a box lock). In some embodiments, the first and second scissors arms 110 and 120 each have a ring handle 112 at the proximal end. The ring handles 112 serve as finger grips. Tissue approximation device 100 can be closed by approximating or bringing together the ring handles 112, which in turn approximates or brings together the distal ends 114 of the first and second scissors arms 110 and 120. In some embodiments, the proximal ends of the first and second scissors arms 110 and 120 comprise straight or curved handles instead of the ring handles 112 to serve as finger grips. For example, as shown in FIG. 3C, the proximal ends the first and second scissors arms 110 and 120 comprise handles similar to the handles of a plier.

In some embodiments, a pivot bearing is mounted at pivot point 115 to form an axis of rotation of the relative movement between the first and second scissors arms 110 and 120 so that the scissors arms can pivot in a normal scissors or forceps fashion. In some embodiments, the pivot bearing is formed as a flanged shaft inserted into the first scissors arm 110 and second scissors arm 120. In some embodiments, the flanged shaft is a screw or a nail. In some embodiments, the flanged shaft has a short head that forms a flange and has a shank or a pin passing through the thickness of the first scissors arm 110 (and/or thickness of the second scissors arm 120) at the location of the pivot point 115. It should be appreciated that the arms of the approximation device can alternately be moved in a different manner than scissors arms, such as pivotably movable by a different kind of attachment or non-pivoting movement such as movement in a parallel orientation.

Figure 3D:
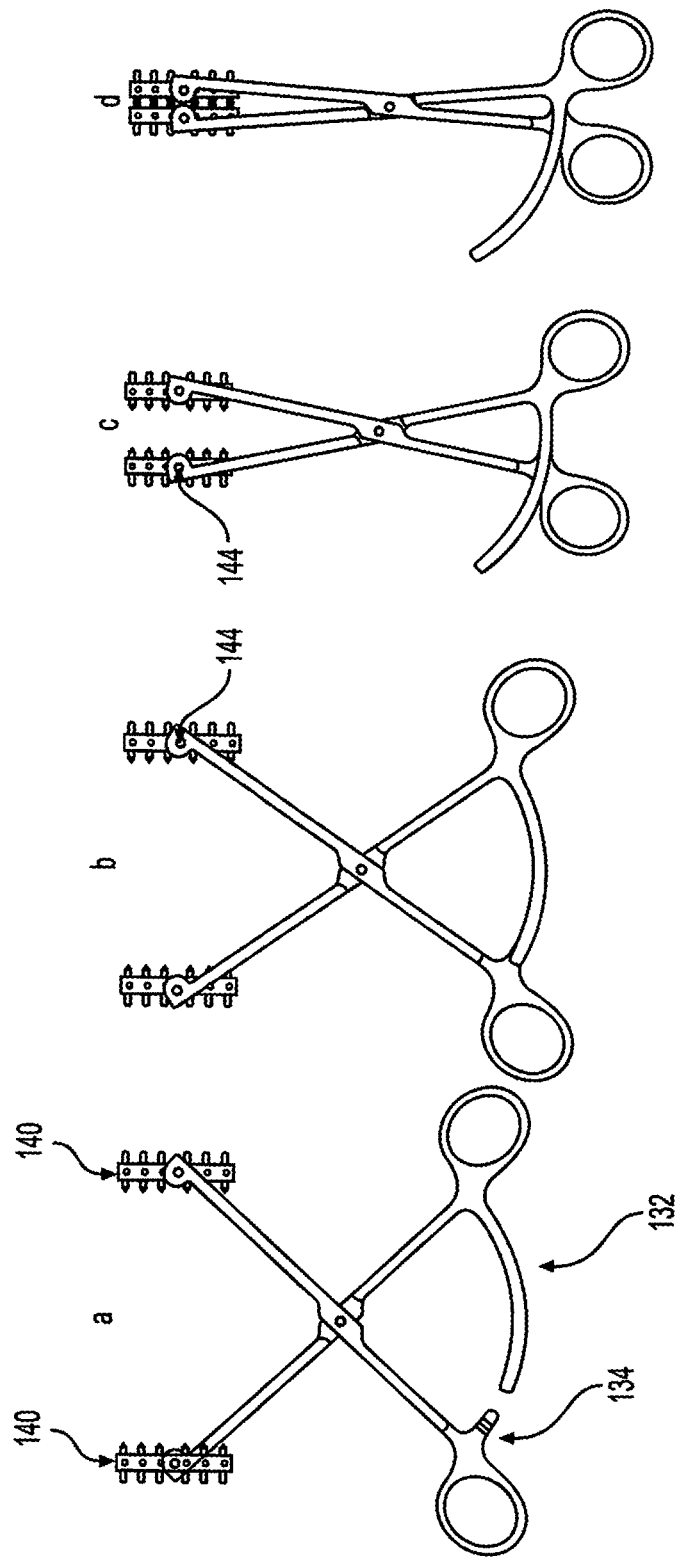
FIG. 3D illustrates the approximation of the distal ends of a first scissors arm and a second scissors arm of the tissue approximation device of FIG. 3A from a fully opened position (a) to a fully closed position (d).

As shown in FIG. 3A, in some embodiments, tissue approximation device 100 includes a ratchet 130 at the proximal ends of the first scissors arm 110 and the second scissors arm 120. The ratchet 130 allows the approximation of the distal ends 114 of the first scissors arm 110 and the second scissors arm 120 to be flexibly adjusted across a range of distance. In some embodiments, as shown in FIG. 3D, the ratchet 130 includes a plurality of successive ratchet teeth 132 and a ratchet catch 134. When the ring handles 112 are brought together, the ratchet catch 134 engages with and moves along the ratchet teeth 132. The ratchet catch 134 can be stopped at a desired position along the ratchet teeth 132. In some embodiments, when the distal ends 114 of the first and second scissors arm 110 and 120 are spaced apart at a desired distance, the engagement of the ratchet catch 134 and the ratchet teeth 132 can be locked. In some embodiments, successive ratchet teeth 132 are spaced apart at a fixed distance from each other. In some embodiments, successive ratchet teeth 132 are closely spaced apart to allow flexible adjustment of the distance between the distal ends 114 of the first and second scissors arm 110 and 120.

In some embodiments, the ratchet 130' is located at or near the end of the proximal ends of the first and second scissors arm 110 and 120. For example, as shown in FIG. 3B, the ratchet 130' is at the end of the ring handles 112'. In some embodiments, instead of the ratchet 130, the tissue approximation device 100 includes a screw locking mechanism 150 for adjustably locking the distance between the distal ends 114 of the first scissors arm 110a and the second scissors arm 120a. In some embodiments, for example, as shown in FIG. 3C, the screw locking mechanism 150 includes a threaded shaft 152. The threaded shaft 152 may have a first end attached to the first scissors arm 110a and a second end that passes through a hole in the second scissors arm 120a. In some embodiments, the screw locking mechanism 150 further includes a locking screw. In some embodiments, the locking screw is threaded and configured to move along the threaded shaft to adjust the distance between the handles of the first and second scissors arms 110a and 120a. It should be appreciated that other mechanisms to retain the arms (and thereby retain the attached tissue engaging members) are also contemplated for the various tissue approximation devices disclosed herein.

In some embodiments, as shown in FIG. 3A, to engage and grip tissue, a rake member 140 is connected to the distal end 114 of the first scissors arm 110. In some embodiments, a rake member 140 is connected to the distal end 114 of the first scissors arm 110 and a clamp member is at the distal end 114 of the second scissors arm 120. The clamp member may be a flat or curved plate integral to, fixedly connected, or removably connected to the distal end 114 of the second scissors arm 120. In some embodiments, two rake members 140 are respectively connected to the distal ends 114 of the first scissors arm 110 and the second scissors arm 120. In some embodiments, the rake members 140 are configured to engage and grip tissue in an atraumatic fashion and bring the two gripped sides of tissue together. As defined herein, a rake member refers to a structural member that is permanently or removably attached to the distal end of a scissors arm, e.g., via an articulating joint, and includes an array of hooks configured to grip tissue. The hooks or the rake members form types of tissue engaging members or tissue gripping members defined herein.

In some embodiments, separating the ring handles 112 separates the rake members 140. In such embodiments, the ring handles 112 are approximated and brought together such that the rake members 140 are brought together to approximate two sides of tissue gripped by the rake members 140. In other embodiments, bringing the ring handles 112 together separates the rake members 140. In such embodiments, the ring handles 112 are moved apart from each together so that the rake members 140 are brought together to approximate the two sides of tissue gripped by the rake members 140.

As shown in FIG. 3A, in some embodiments, the rake member 140 includes one or more hooks 142 to grip or "bite" the tissue. In some embodiments, each hook 142 on the rake member 140 of the first scissors arm 110 corresponds to a hook 142 on the rake member 140 of the second scissors arm 120. For example, each hook 142 on the rake member 140 of the first scissors arm 110 is opposite to a hook 142 on the rake member 140 of the second scissors arm 120 to grip two opposite sides of tissue. The hooks 142 can be directly opposite or alternatively staggered so opposing hooks are offset. In some embodiments, the hooks 142 are distributed in a linear fashion on the rake member 140. In some embodiments, the hooks 142 are distributed in two dimensions on the rake member 140. In such embodiments, the hooks 142 may be distributed in a plurality of rows, and in some embodiments in a plurality of staggered rows.

As described herein, any suitable number of hooks 142 may be mounted on the rake member 140. For example, the number of hooks 142 may be any number equal to or greater than two, e.g., two, three, four, five, six, seven, eight, etc. The number of hooks 142 may be determined based on the length of the rake member 140, the dimension of the hooks and the distance between the hooks 142, which may be determined based on various considerations, such as the type, size, and/or location of the tissue to be gripped.

The hook 142 may have any suitable shape, size, and cross-section that allow the hook 142 to effectively grip the tissue, but not cut or slice through the tissue as the hook 142 applies pressure on it. In some embodiments, the hook 142 has an elongated body. The elongated body can be straight or curved. In some embodiments, the hook 142 has a cross-section with a curved or smooth circumference. In some embodiments, the hook 142 has a cross-section without a sharp edge. In some embodiments, the hook 142 has a cross-section without a cutting edge. For example, in some embodiments the hook 142 has a cross-section having a circular or elliptical circumference. In some embodiments, the hook 142 has a pointed tip. In some embodiments, the pointed tip is a cone-shaped pointed tip. In some embodiments, the hook 142 has a blunt or a semi-blunt tip. In some embodiments, the cross-section of the hook 142 is dimensioned to prevent the hook 142 from cutting through the tissue. In some embodiments, the diameter of the cross-section of the hook 142 ranges from 0.8 mm to 1.5 mm.

Figure 5B:
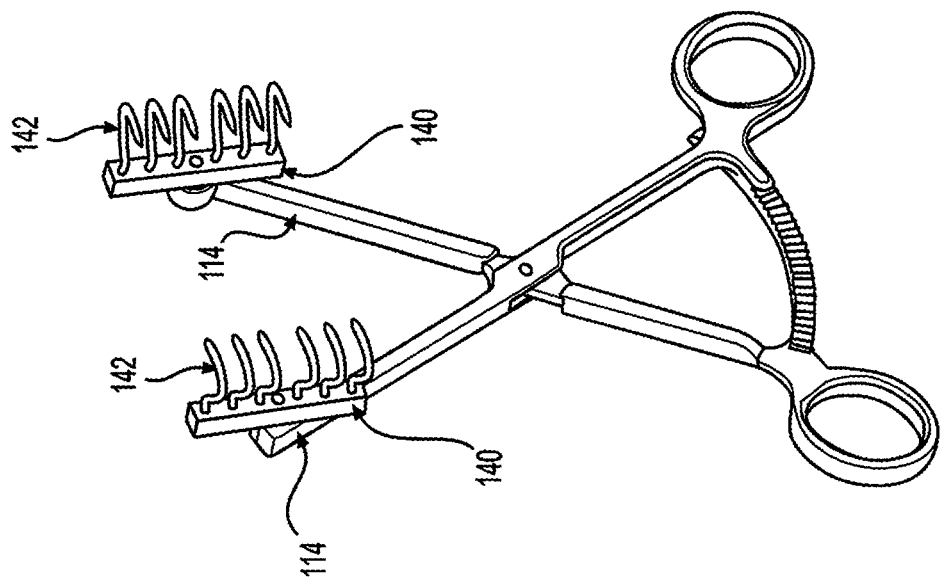
FIG. 5B illustrates a perspective view of the exemplary tissue approximation device of FIG. 5A.
Figure 5A:
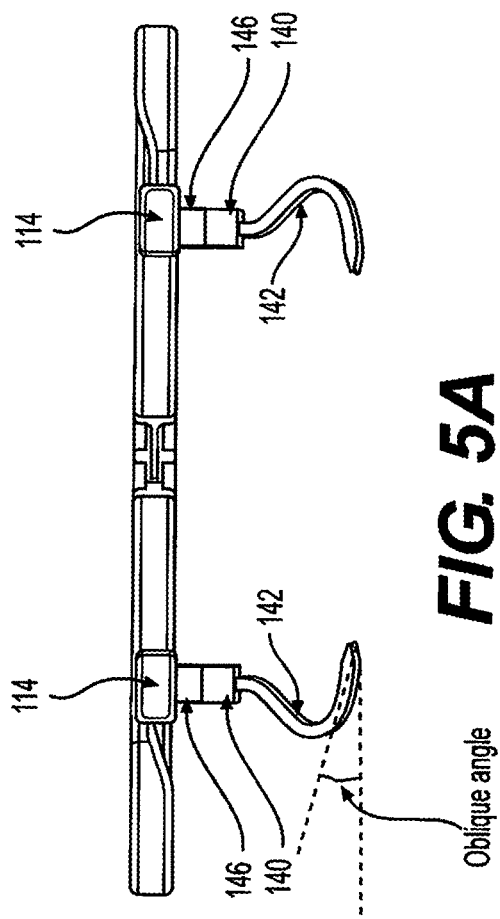
FIG. 5A illustrates a front view of an exemplary tissue approximation device, according to some embodiments of the present disclosure.

FIG. 4A illustrates a front view of tissue approximation device 100, according to some embodiments of the present disclosure. FIG. 4B illustrates a perspective view of the tissue approximation device 100 of FIG. 4A. FIG. 5A illustrates a front view of another exemplary tissue approximation device 100, according to some embodiments of the present disclosure. FIG. 5B illustrates a perspective view of the exemplary tissue approximation device of FIG. 5A.

As shown in FIGS. 4A-5B, in some embodiments, a portion of the elongated body of the hook 142 is curved or bent. In some embodiments, the entire length of the elongated body of the hook 142 is curved or bent. In some embodiments, as shown in FIGS. 4A and 5B, the curved or bent shape of the elongated body of the hook 142 allows the pointed tip of the hook 142 to penetrate and/or "bite" the tissue at an oblique angle. As defined herein and shown in FIG. 5A, the term "oblique angle" refers to the angle at which the hook 142 penetrates tissue to the plane of the first and second scissors arms 110 and 120.

In some embodiments, the curved or bent shape of the elongated body of the hook 142 allows the hook 142 to have a cupping effect to effectively grip the tissue. In some embodiments, as shown in FIGS. 4A and 5A, the shape of the elongated body of the hook 142 is designed in the shape of an inverted question mark. In some embodiments, the hook 142 is designed in the shape of the letter "C." The opening of the "C" may be tilted at different angles relative to the plane of the tissue being gripped. In some embodiments, the oblique angle of penetration allows the hook 142 to penetrate and grip the tissue, but not to tangentially scratch, and not to cut through or rip the tissue. In some embodiments, the oblique angle of penetration prevents the pointed tip of the hook 142 from penetrating the tissue perpendicularly wherein hook 142 may act like a straight rod tearing through the tissue. In some embodiments, the oblique angle of penetration further prevents the pointed tip of the hook 142 from perpendicularly penetrating and gripping the tissue with excessive torque, which may bend the hook 142 outward and cause it to pull out of the tissue, failing its attempt to bring the tissue together. In some embodiments, the oblique angle ranges from 15 degrees to 70 degrees. In some embodiments, as shown in FIGS. 4A and 5A, a hook 142 on the rake member 140 of the first scissors arm 110 and a corresponding hook 142 on the rake member 140 of the second scissors arm 120 form a pair and are curved inwardly towards each other.

Figure 6:
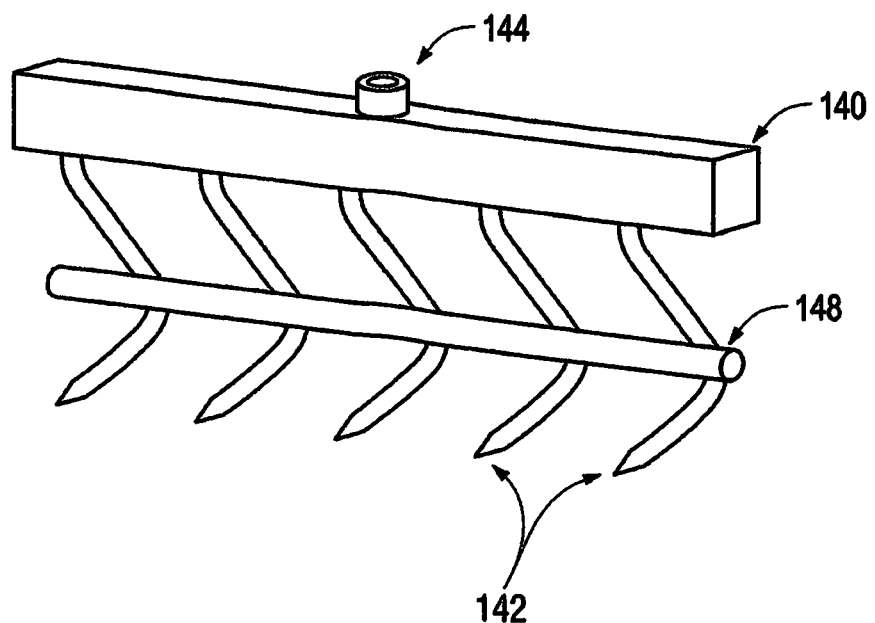
FIG. 6 illustrates a perspective view of an exemplary rake member of an exemplary tissue approximation device, according to some embodiments of the present disclosure.

FIG. 6 illustrates a perspective view of an exemplary rake member 140, according to some embodiments of the present disclosure. As shown in FIG. 6, in some embodiments, an elongated transverse bar 148 connects the hooks 142 mounted on the rake member 140. The transverse bar 148 may be a rod or a tube. The transverse bar may be made of metal, plastic, or rubber and attached to the hooks by various methods. The bar can be circular, rectangular, or other shapes in cross section. It can be attached on the inner curve or the outer curve of the hook members. In some embodiments, the transverse bar 148 connects to the hooks 142 at the elbow flexion of the hooks 142. In some embodiments, the transverse bar 148 forms a ridge on the hooks 142 and limits the penetration of the hooks 142 into the tissue. In some embodiments, when the hooks 142 penetrate the tissue, the transverse bar 148 functions as a stop and rests against the surface of the tissue. The transverse bar 148 may relieve the tension on the hooks 142 penetrating and gripping the tissue by transferring and distributing the tension more evenly over a wider surface contacting the tissue. The transverse bar 148 can be used in any of the embodiments of the rake members or hooks described herein.

In some embodiments, instead of connecting to the transverse bar 148, the hook 142 has a thickened portion along its shaft that functions as a stop to limit the penetration of the hook 142 into the tissue. In some embodiments, the thickened portion is a section along the length of the hook 142. The thickened portion may be in any suitable shape, such as a ball, a ridge, or a bar. In some embodiments, the thickened portion is formed by connecting to a separate member, such as a ball, a ridge, or a bar. The thickened portion may be placed at any suitable location along the length of the hook 142. In some embodiments, the thickened portion is formed at the elbow flexion of the hooks 142. In some embodiments, each of the hooks 142 of the rake member 140 includes a thickened portion. Such thickened portion can be used in any of the embodiments of the rake members or hooks described herein.

The hook 142 and rake member 140 may be made of any suitable medical grade material. The rake member 140 may be disposable, replaceable, and reusable. In some embodiments, the rake member 140 comprises a locking mechanism that allows it to be released (removed) and replaced on the scissors arm. In some embodiments, the rake member 140 may be repeatedly disinfected and sterilized or disposable and replaced by another hook arm. The hook 142 may be disposable, replaceable, and reusable. In some embodiments, the hook 142 may be repeatedly disinfected and sterilized. In some embodiments, the rake member 140 and/or the hook 142 are made of surgical stainless steel. In some embodiments, the rake member 140 and/or hook 142 are made of surgical carbon steel. In some embodiments, the rake member 140 and/or hook 142 are made of medical grade polymeric material. Removable and replaceable rake members and/or hooks enable different types, configurations and sizes of hooks to be substituted.

It should be appreciated that any of the versions of the hooks and rakes of the present disclosure can be applied to any of the embodiments of the tissue approximation devices disclosed herein.

In some embodiments, as shown in FIG. 3A, the distal end 114 of the first scissors arm 110 is connected to a rake member 140 via an articulating joint 144. In some embodiments, each of the distal ends 114 of both the first scissors arm 110 and the second scissors arm 120 is connected to a rake member 140 via an articulating joint 144. In some embodiments, articulating joint 144 is a hinge joint or a pivot joint at the tip of distal end 114. FIG. 3D illustrates the approximation of the distal ends 114 of the first scissors arm 110 and the second scissors arm 120 from a fully opened position (a) to a fully closed position (d). As illustrated in FIG. 3D, as the distal ends 114 of the first scissors arm 110 and the second scissors arm 120 approximate, the articulating joints 144 allow the rake member 140 connected to the first scissors arm 110 and the rake member 140 connected to the second scissors arm 120 to stay parallel to each other and stay perpendicular to the direction of approximation. In some embodiments, the articulating joints 144 allow the wound edges to stay parallel while the first scissors arm 110 and the second scissor arm 120 are approximated at an angle.

In some situations, the articulating joints 144 may reduce or prevent the rake member 140 of the first scissors arm 110 and the rake member 140 of the second scissors arm 120 from forming a wedge are that pinches the tissues at a variable angle in a scissor like fashion when the distal ends 114 of the first scissors arm 110 and the second scissors arm 120 approximate.

As shown in the front views of the exemplary tissue approximation device 100 of FIGS. 4A and 5A, in some embodiments, the hooks 142 and rake members 140 are in a plane below first and second scissors arms 110 and 120. Such configuration allows the other portions of tissue approximation device 100 to be out of the plane of the tissue being gripped and approximated by the hooks 142 and rake members 140. Such configuration further allows flexibility in adjusting the position of the tissue being gripped and approximated.

In some embodiments, as shown in FIGS. 4A and 4B, the distal ends 114 are curved and deviate from the plane of the other portions of first scissors arm 110 and second scissors arm 120. In such embodiments, as shown in FIG. 4A, the curved distal ends 114 position the rake members 140 below the plane of the other portions of the first scissors arm 110 and the second scissors arm 120. In some embodiments, the curved distal ends 114 position the hooks 142 and rake members 140 in a plane 1.5 cm to 4 cm below the plane of the first scissors arm 110 and the second scissors arm 120. For example, the curved distal ends 114 may position the hooks 142 and/or rake members 140 in a plane 1.5 cm, 2 cm, 2.5 cm, 3 cm, or 3.5 cm below the plane of the first scissors arm 110 and the second scissors arm 120. In some embodiments, the curved distal ends 114 enable adjusting the gripping or the position of the gripping of the tissue without interference from other portions of the tissue approximate device 100.

In some embodiments, as shown in FIGS. 5A and 5B, the distal ends 114 are flat and are in the same plane as the other portions of the first scissors arm 110 and second scissors arm 120. In such embodiments, as shown in FIG. 5A, the tissue approximation device 100 may further include vertical extension members 146 that protrude from the distal ends 114 of the first and second scissors arms 110 and 120 in a direction perpendicular to the plane of the distal ends 114. The vertical extension members 146 position the rake members 140 below the plane of the first scissors arm 110 and the second scissors arm 120. In some embodiments, the vertical extension members 146 position the hooks 142 and rake members 140 in a plane 1.5 cm to 4 cm below the plane of the first scissors arm 110 and the second scissors arm 120. For example, the vertical extension members 146 may position the hooks 142 and/or rake members 140 in a plane between about 1.5 cm to about 3.5 cm, e.g., 1.5 cm, 2 cm, 2.5 cm, 3 cm, or 3.5 cm below the plane of the first scissors arm 110 and the second scissors arm 120. The vertical extension members 146 further allow adjusting the gripping or the position of the gripping of the tissue without interference from other portions of the tissue approximation device 100.

FIGS. 7-11 illustrate an alternate embodiment of the tissue approximation device of the present disclosure. The tissue approximation device is designated general by reference numeral 160 and differs from device 100 in that it has a transverse bar which maintains the parallel orientation and movement of the rake members.

More specifically, device 100 has a first arm 162 having a distal end 162a and a second arm 164 having a distal end 164a. The arms 162, 164 are connected at pivot point 166 and move in a scissors like fashion. Similar to device 100, arm 162 has a ring handle 168 and arm 164 has a ring handle 170 to serve as grips for the user to move, e.g. pivot, the arms 162, 164. Note in device 100 and device 160, a pin 115 or 166 connects the arms and provides for pivotal movement, however, it is also contemplated that the arms can be connected in other ways for pivotal movement or can move in other fashions, e.g., they can move in parallel rather than pivot.

Figure 7:
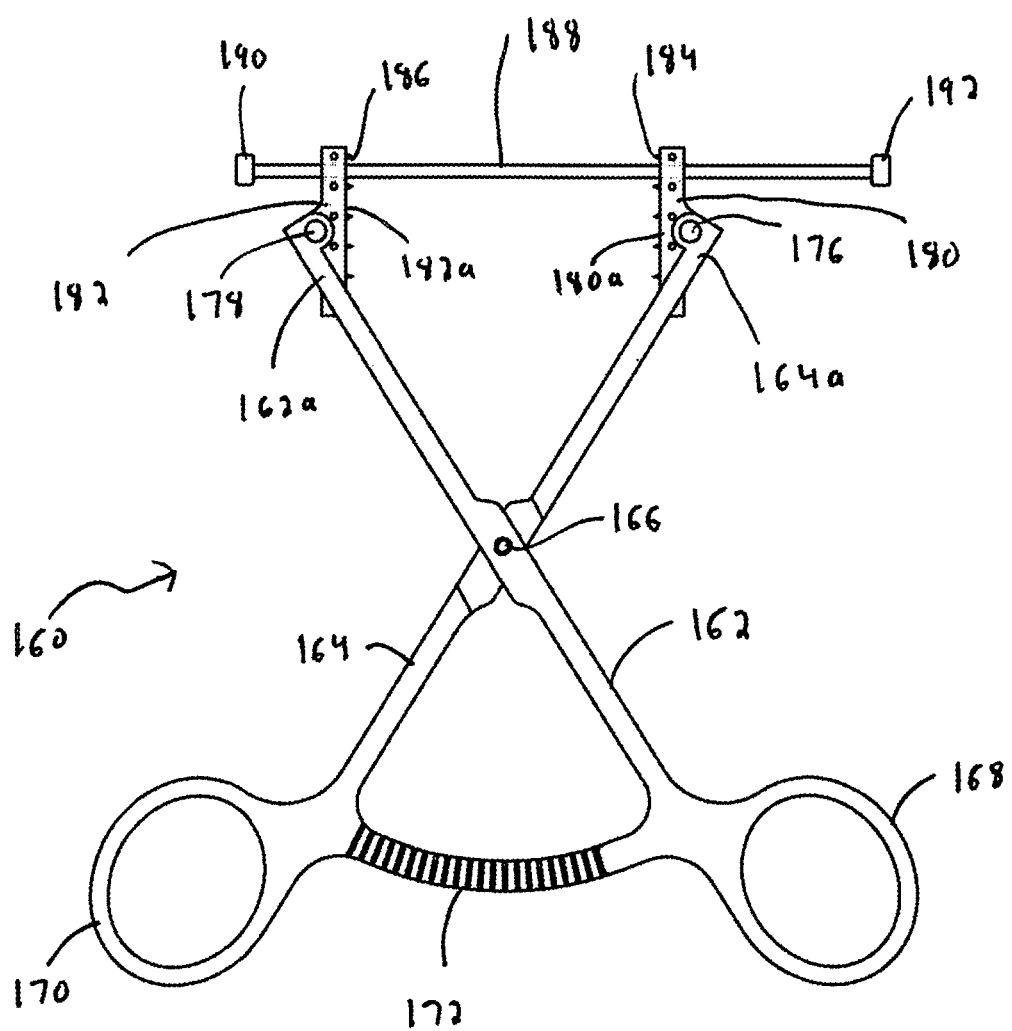
FIG. 7 illustrates an alternate embodiment of the tissue approximation device of the present disclosure.
Figure 8:
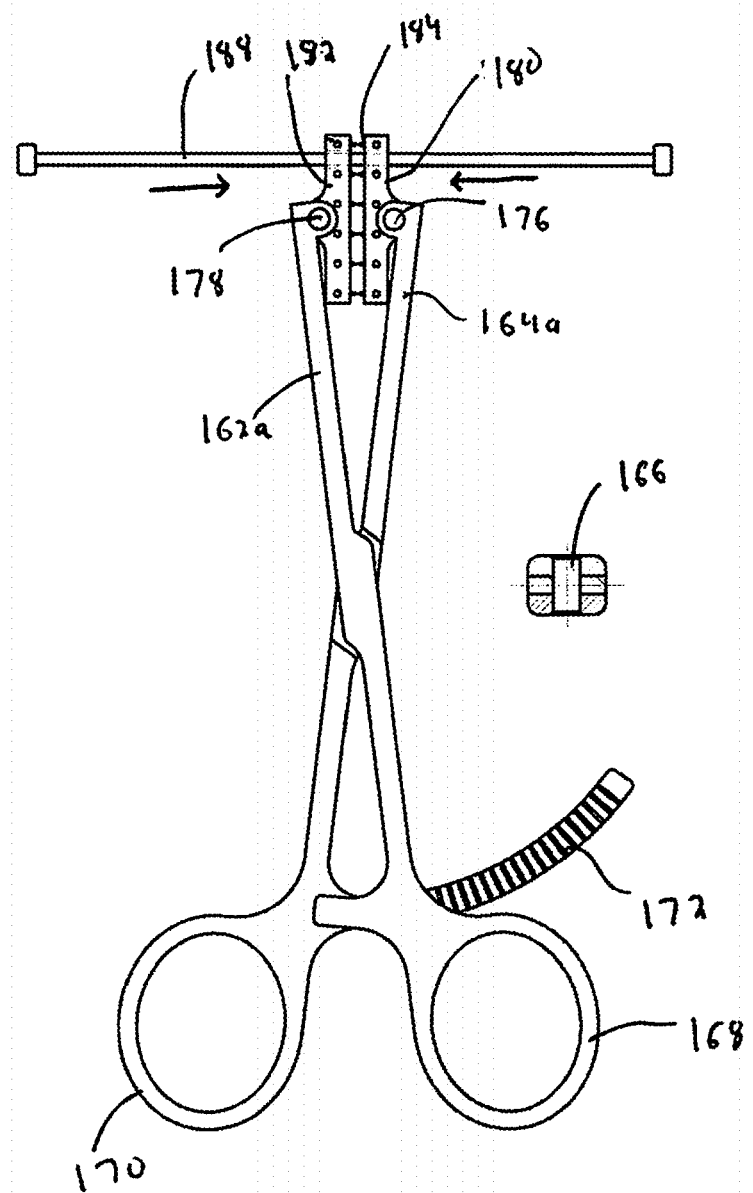
FIG. 8 illustrates the approximation of the distal ends of a first arm and a second arm of the tissue approximation device of FIG. 7 from a fully opened position to a fully closed position.

Connected to the distal end 162a of arm 162 is first rake member 182 and connected to the distal end 164a of arm 164 is second rake member 180. ("First" and "second" are used throughout the disclosure for ease of reference). Rake members 180, 182 are similar to the two rake members 140 of device 100, except they include a channel to receive a transverse bar 188. The channel 181 can be seen in the cross-sectional view of FIG. 11 and is dimensioned to receive the transverse bar 188 for slidable movement therein. A coating 196 such as Teflon (PTFE) for example can be provided within the channel 181 to constrain the transverse bar 188 to facilitate movement of the rake members 182, 180 over the transverse bar 188. The coating within the first and second channels of the respective first and second rake members 180, 182 is engageable by the transverse bar 188 such that the coating constrains the transverse bar 188 and prevents a wedging effect that could impair smooth gliding through the channels. Other coating materials that can facilitate friction free gliding and perpendicular alignment are also contemplated. The coating 196 also provides a grip/retention on the transverse bar 188. As the arms 162, 164 are closed, the rake members 182, 180 can slide over the transverse bar 188 as the channel slidably moves over the bar 188. The distance of travel of the rake members 180, 182 is dependent on the extent of movement of the arms 162, 164. That is, as the arms 162, 164 are closed, i.e., pivoted toward each other as ring members 168, 170 are moved toward each other, the rake members 180, 182 move toward each other to close (decrease) a distance between the rake members 180, 182. The fully closed distance is illustrated in FIG. 8 with the arrows indicating the direction of movement. When the arms 162, 164 are moved away from each, i.e., pivoted away each other as ring members 168, 170 are moved away from each other, the distance between the rake members 180, 182 is increased. (The fully opened position is shown in FIG. 7). A ratchet 172 can be provided to retain the position of the arms 162, 164 in the same manner as the ratchet described above. Other mechanisms for retaining the position of the arms 162, 164 are also contemplated in the various embodiments disclosed herein.

Figure 12:
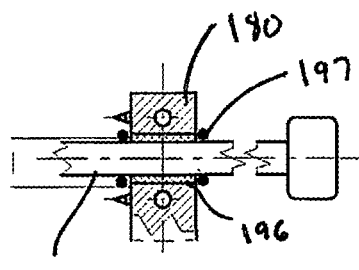
FIG. 12 is a cross-sectional view similar to FIG. 11 showing an alternative embodiment having rollers to constrain the transverse bar.
Figure 13:
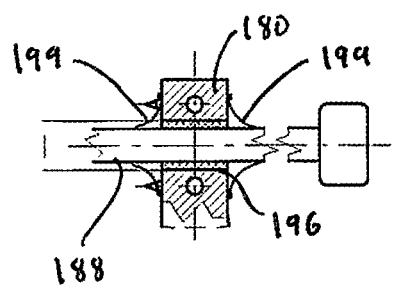
FIG. 13 is a cross-sectional view similar to FIG. 11 showing an alternative embodiment having guide springs to constrain the transverse bar.

FIGS. 12 and 13 illustrate alternative embodiments for retaining/constraining the transverse bar 188 with respect to the channel of the rake members and enabling smooth gliding. In FIG. 12 a plurality of rollers 197 are provided. The rollers can be positioned within the channel of the rake members to engage, constrain and provide friction free gliding of the transverse bar 188. Alternatively, they can be positioned outside the channel to engage the transverse bar 188 outside the channel as shown in FIG. 12. In FIG. 13, a plurality of guide springs 199 are provided. The springs 199 can be positioned within the channel of the rake members to constrain the transverse bar 188. Alternatively, they can be positioned outside the channel to engage and constrain the transverse bar outside the channel, as shown in FIG. 13. The springs 199 similarly prevent wedge locking that could limit even gliding. The spring members can be utilized alone or utilized with the rollers and/or with the coating. The rollers can be utilized alone or utilized with the spring members and/or with the coating. In other embodiments, a plurality of rollers are provided in or outside the channel to engage, constrain and provide friction free gliding of the transverse bar. A plurality of springs can be provided in or adjacent the channel in lieu of or in addition to the rollers to engage/constrain the transverse bar and similarly prevent wedge locking that could limit even gliding. In each of these embodiments, the first and second rake members can move toward each other along the transverse bar in a parallel orientation.

In another embodiment, the transverse bar could be rectangular shape and have small cylinders on the bar that would provide for gliding of the rake members over the transverse bar received in the channel of the rake members.

Referring back to the transverse bar of FIGS. 7-11, the transverse bar 188 maintains the parallel movement of the rake members 180, 182 as it prevents the rake members 180, 182 from flipping or re-orienting from their parallel position. More specifically, as shown, the rake members 180, 182 are mounted to the respective arms 164, 162 so they face each other with their longitudinal axes parallel to one another. The rake members 180, 182 in the illustrated embodiment are shown mounted to the arms 164, 162 at a mid portion and receiving the transverse bar 188 at a distal portion. The transverse bar 188 is perpendicular to the longitudinal axis of the rake members 180, 182. In this manner, the rake members 180, 182 can maintain their parallel position (inner surfaces 180a, 182a facing each other) during their travel along the bar as they approximate tissue (via their respective series of hooks 184, 186).

The rake members 180, 182 have a plurality of tissue engaging members as in the rake members 140 described above. As shown, rake member 180 has a plurality of tissue engaging (penetrating) members in the form of needles or hooks 184 and rake member 182 has a plurality of tissue engaging (penetrating) members in the form of needles or hooks 186. The hooks 184, 186 are retained in a channel of the respective rake member as shown in the cross-sectional view of FIG. 9A. The hooks 184, 186 can have a curve or bend at region 184a. An elongated transversely extending bar 194 attached to hooks 184, 186, like bar 148 of FIG. 6 described above, can be provided to act as stop for tissue penetration of the hooks 184, 186. FIG. 9A also illustrates the pin 176 (with washer 177) through the arm 164 for attaching the rake member 180 to arm 164. Rake member 82 can be attached to arm 162 in a similar manner.

The use of the tissue approximating device in conjunction with the meshing device will now be described. The system/method of the approximation and meshing can in some embodiments be used for a progressive closure of the wound.

The method for closing a wound will be described utilizing the device 160, it being understood that device 100 (as well as alternatives of device 100 and device 160) would be used in a similar manner and thus the described method is fully applicable to the device 100 and the alternative configurations of devices 160 and 100.

The method comprises first placing the tissue approximation device 160 (or 100) adjacent a wound so the first rake member 182 extending from the first arm 162 is positioned on a first side of the wound and the second rake member 180 extending from the second arm 164 is positioned on a second side of the wound. In this position, the first and second rake members are spaced a first distance X from each other.

Next, the first and second arms 162, 164 are moved toward each other to move the rake members 180, 182 toward each other in a parallel movement so the inner surfaces 180a, 182a of the respective rake member 180, 182 are spaced apart a closer distance, i.e. a distance Y from each other which is less than the distance X. The transverse bar 188, in the embodiments where provided, maintains the parallel movement of the rake members 180, 182. The rake members 180, 182 thus place the tissue in tension as the tissue is approximated.

Next, the meshing device, which includes at least one penetrating or puncturing member, is inserted into the tissue outside the area between the rake members 180, 182, i.e., external of an outer surface of the rake members 180, 182. The meshing device of FIGS. 2A-2E described above is one type of meshing device that can be utilized.

If further wound closure (tissue approximation) is necessary or desirable subsequently or at a later time, after the meshing device is applied to the tissue to apply the slits as described above, the first and second arms of the device 160 are closed to move the rake members 180, 182 closer toward each other, with the distance between inner surfaces 182a, 182a decreasing to a distance Z which is less than distance Y. Then the meshing device is again applied to the tissue outside the region of the rake members. This can continue as the rake members 180, 182 are again moved toward each other, followed by meshing. Note that the locking ratchet mechanism has enough excursion to allow for gradual tightening as the tension is released by the mesh expansion effect. This repeated/progressive rake movement (tissue tensioning) and meshing can in some embodiments be continued progressively until the wound edges are sufficiently closed. At this close distance, in some embodiments, a suture can then be applied to close off the wound without the need for a skin graft to thereby reduce scarring.

In some embodiments, in addition to or instead of using the tissue approximation device 100 or 160, internally induced tumescence is performed to place a tissue under tension for performing PME. In some embodiments, internally induced tumescence is achieved by injecting a material into the tissue in the area of interest. The material may include normal physiologic solutions, regenerative reagents, a suspension of cells, a tissue graft, or a selected combination thereof. In some embodiments, injecting the material separates the native fibers in the tissue, thereby generating a fibrous vascularized scaffold with interstices that can be filled by new tissue generated from the natural regenerative process of tissue. In some embodiments, a material having regenerative potential is injected into the interstices to further promote tissue regeneration and expansion.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. Moreover, while illustrative embodiments have been described herein, the scope of the disclosure includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive.

It is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as exemplary only, with a true scope and spirit of the disclosed embodiments being indicated by the following claims.

Throughout the present disclosure, terms such as "approximately," "generally," "substantially," and the like should be understood to allow for variations in any numerical range or concept with which they are associated. For example, it is intended that the use of terms such as "approximately" and "generally" should be understood to encompass variations on the order of 25% (e.g., to allow for manufacturing tolerances and/or deviations in design).

Although terms such as "first," "second," "third," etc., may be used herein to describe various operations, elements, components, regions, and/or sections, these operations, elements, components, regions, and/or sections should not be limited by the use of these terms in that these terms are used to distinguish one operation, element, component, region, or section from another. Thus, unless expressly stated otherwise, a first operation, element, component, region, or section could be termed a second operation, element, component, region, or section without departing from the scope of the present disclosure.

Each and every claim is incorporated as further disclosure into the specification and represents embodiments of the present disclosure. Also, the phrases "at least one of A, B, and C" and "A and/or B and/or C" should each be interpreted to include only A, only B, only C, or any combination of A, B, and C.

What is claimed is:

1. A tissue approximation device comprising:
   a first arm having a proximal end and a distal end;
   a second arm having a proximal end and a distal end, the second arm connected to the first arm;
   a first rake member connected to the distal end of the first arm, the first rake member having a longitudinal axis and a first plurality of tissue engaging members extending therefrom to engage tissue;
   a second rake member attached to the distal end of the second arm, the second rake member having a longitudinal axis second plurality of tissue engaging members extending therefrom to engage tissue; and
   a transverse bar extending through the first and second rake members and positioned perpendicular to the longitudinal axis of the first and second rake members, the first and second rake members slidable along the transverse bar and movable toward each other in a parallel movement.

2. The tissue approximation device of claim 1, wherein the first rake member is connected to the distal end of the first arm via a first articulating joint and the second rake member is connected to the distal end of the second arm via a second articulating joint.

3. The tissue approximation device of claim 1, wherein the first rake member and the second rake member are movable towards each other along the transverse bar in parallel to move tissue edges closer together as the distal ends of the first arm and the second arm approximate.

4. The tissue approximation device of claim 1, wherein the first and second arms are pivotably connected and move in scissors-like fashion.

5. The tissue approximation device of claim 1, wherein the first and second plurality of tissue engaging members each comprise a plurality of hooks having an elongated body and at least a portion of the elongated body is curved.

6. The tissue approximation device of claim 5, further comprising a second bar, wherein the second bar is spaced from tips of the plurality of hooks to provide a stop for tissue penetration of the plurality of hooks.

7. The tissue approximation device of claim 6, wherein the second bar is parallel to the transverse bar.

8. The tissue approximation device of claim 6, wherein the second bar connects to the plurality of hooks at an elbow.

9. The tissue approximation device of claim 1, wherein the first rake member includes a first channel and the second rake member includes a second channel, the transverse bar extending through the first and second channels and maintaining a parallel orientation of the first and second rake members as the first and second rake members slide along the transverse bar toward each other to approximate tissue.

10. The tissue approximation device of claim 9, further comprising a coating within the first and second channels engageable by the transverse bar.

11. The tissue approximation device of claim 1, further comprising a plurality of roller members engageable with the transverse bar to constrain the transverse bar.

12. The tissue approximation device of claim 1, further comprising a plurality of spring elements engageable with the transverse bar to constrain the transverse bar.

13. The tissue approximation device of claim 1, wherein the transverse bar has a first diameter and enlarged opposing ends have a diameter greater than the first diameter.

14. A system for closing a wound comprising:
   a) a tissue approximation device configured to apply tension to tissue in an area adjacent the wound, the tissue approximation device comprising:
      a first arm having a proximal end and a distal end;
      a second arm having a proximal end and a distal end, the second arm being connected to the first arm;
      a first rake member connected to the distal end of the first arm and having a first plurality of tissue members extending therefrom configured to penetrate and grip tissue on a first side of the wound; and
      a second rake member connected to the distal end of the second arm and having a second plurality of tissue engaging members extending therefrom configured to penetrate and grip tissue on a second side of the wound;
      wherein the first and second arms are movable to move the first and second rake members toward each other in a parallel movement to adjust a distance between the first and second rake members to approximate tissue; and
   b) a meshing device having a supporting frame and a plurality of puncturing devices configured to puncture the tissue, the meshing device puncturing tissue outside a region of tissue defined between the first and second rake members.

15. The system of claim 14, wherein the tissue approximation device includes a transverse bar extending through the first and second rake members, the first and second rake members movable in the parallel movement along the transverse bar.

16. The system of claim 15, wherein the first rake member includes a first channel and the second rake member includes a second channel, the transverse bar extending through the first and second channels and maintaining a parallel orientation of the first and second rake members as the first and second rake members slide along the transverse bar toward each other to approximate tissue.

17. The system of claim 16, wherein the transverse bar is constrained by a coating in the channel.

* * * * *